(12) United States Patent
Leeflang et al.

(10) Patent No.: US 9,421,316 B2
(45) Date of Patent: Aug. 23, 2016

(54) APPARATUS AND METHODS FOR ACCESSING THE LYMPHATIC SYSTEM

(76) Inventors: Stephen A. Leeflang, Sunnyvale, CA (US); Christian S. Eversull, Palo Alto, CA (US); Matthew J. Callaghan, Stanford, CA (US)

( * ) Notice: Subject to any disclaimer, the term of this patent is extended or adjusted under 35 U.S.C. 154(b) by 475 days.

(21) Appl. No.: 13/100,297

(22) Filed: May 3, 2011

(65) Prior Publication Data
US 2011/0276023 A1 Nov. 10, 2011

Related U.S. Application Data

(60) Provisional application No. 61/330,882, filed on May 4, 2010, provisional application No. 61/330,885, filed on May 4, 2010.

(51) Int. Cl.
*A61M 37/00* (2006.01)
*A61M 1/34* (2006.01)
*A61M 1/36* (2006.01)

(52) U.S. Cl.
CPC ............. *A61M 1/3496* (2013.01); *A61M 1/367* (2013.01); *A61M 2202/0405* (2013.01)

(58) Field of Classification Search
CPC ............. A61M 1/3496; A61M 1/367; A61M 2202/0405
USPC .................................................. 604/500, 319
See application file for complete search history.

(56) References Cited

U.S. PATENT DOCUMENTS

| | | | | |
|---|---|---|---|---|
| 3,916,875 A * | 11/1975 | Toch | ............................. | 600/431 |
| 4,581,017 A * | 4/1986 | Sahota | ..................... | 604/101.01 |
| 4,646,742 A * | 3/1987 | Packard et al. | ............... | 606/194 |
| 4,957,484 A * | 9/1990 | Murtfeldt | ...................... | 604/540 |
| 5,158,536 A * | 10/1992 | Sekins | .................... | A61F 7/123 |
| | | | | 128/898 |
| 5,300,022 A * | 4/1994 | Klapper et al. | .................. | 604/35 |
| 5,391,143 A * | 2/1995 | Kensey | ........................ | 604/5.03 |
| 5,766,151 A * | 6/1998 | Valley et al. | ............. | 604/103.07 |
| 5,769,821 A * | 6/1998 | Abrahamson et al. | ........ | 604/104 |
| 5,795,332 A * | 8/1998 | Lucas et al. | ............. | 604/103.06 |
| 6,066,100 A * | 5/2000 | Willard et al. | ................ | 600/452 |
| 6,309,379 B1 * | 10/2001 | Willard et al. | ................ | 600/467 |

(Continued)

FOREIGN PATENT DOCUMENTS

WO 2010080717 A1 7/2010

OTHER PUBLICATIONS

Pflug et al. The Valves of the Thoracic Duct At the Angulus Venosus, 1968M Brit. J. Surg, vol. 55, No. 12, pp. 911-916.*

*Primary Examiner* — Edelmira Bosques
(74) *Attorney, Agent, or Firm* — Vista IP Law Group LLP; William English

(57) ABSTRACT

Systems and methods are provided for performing a medical procedure within a patient's body that involves a thoracic duct including an ostium communicating with the patient's venous system. A distal end of a catheter is introduced through the patient's venous system into a body lumen adjacent the ostium of the thoracic duct. An expandable member on the distal end of the tubular may be expanded adjacent the ostium, e.g., within the body lumen or the thoracic duct itself, and used to isolate the thoracic duct from the body lumen, whereupon a medical procedure may be performed via the thoracic duct. For example, lymphatic fluid may be removed from the thoracic duct through a lumen of the tubular member and/or one or more agents may be introduced into the thoracic duct through the tubular member.

27 Claims, 4 Drawing Sheets

(56) References Cited

U.S. PATENT DOCUMENTS

| | | | |
|---|---|---|---|
| 6,547,775 B1 * | 4/2003 | Blyakhman | 604/505 |
| 6,558,349 B1 * | 5/2003 | Kirkman | 604/104 |
| 6,884,228 B2 * | 4/2005 | Brown et al. | 604/6.01 |
| 7,935,094 B2 * | 5/2011 | Lonky | 604/320 |
| 8,409,214 B2 * | 4/2013 | Lonky et al. | 606/123 |
| 2006/0100658 A1 | 5/2006 | Obana et al. | |
| 2007/0032754 A1 * | 2/2007 | Walsh | 602/2 |
| 2007/0282382 A1 * | 12/2007 | Shuros et al. | 607/17 |
| 2008/0009719 A1 * | 1/2008 | Shuros et al. | 600/427 |
| 2008/0140000 A1 | 6/2008 | Shuros et al. | |
| 2008/0234556 A1 * | 9/2008 | Brooke et al. | 600/301 |
| 2009/0228059 A1 * | 9/2009 | Shuros et al. | 607/17 |

* cited by examiner

APPARATUS AND METHODS FOR ACCESSING THE LYMPHATIC SYSTEM

This application claims benefit of provisional application Ser. No. 61/330,882, filed May 4, 2010, and 61/330,885, filed May 4, 2010, the entire disclosures of which are expressly incorporated by reference herein.

FIELD OF THE INVENTION

The present invention relates generally to apparatus and methods used to perform medical procedures, and, more particularly, to devices, systems, and methods for accessing the lymphatic system of a patient, e.g., to remove, separate, and/or re-infuse lymphatic fluid.

BACKGROUND

The lymphatic system includes a network of vessels generally separate from veins and arteries. Rather than whole blood, the lymphatic vessels carry lymphatic fluid (or lymph). The lymphatic system serves a variety of physiologic purposes, including returning interstitial fluid to the vascular space, transporting fats from the digestive tract, and transporting immune-mediating cells. The composition of lymphatic fluid is similar to plasma. It contains white blood cells, but generally does not contain red blood cells, platelets, or various other components of whole blood. The lymphatic system may be involved in a variety of pathologic states, including lymphatic obstruction leading to lymphedema, leakage of lymphatic fluid, which may lead to chylothorax, or the invasion and spread of malignant cells leading to metastasis. The lymphatic system is involved in nearly any immune mediated response, whether to infectious agents (e.g., viruses, bacteria, parasites, etc.), malignancy, or in the setting of auto-immune disorders. The lymphatic system may serve as a repository for infected cells in disorders such as HIV or may contain a higher concentration of malfunctioning cells in various immune system disorders. To achieve diagnosis and/or treatment of these and other conditions, it may be desirable to access the lymphatic system.

SUMMARY

The present invention is directed generally to apparatus, systems, and methods for performing medical procedures, and, more particularly, to apparatus, systems, and methods for accessing the lymphatic system of a patient, e.g., to remove, separate, and/or re-infuse lymphatic fluid.

Historically, the lymphatic vessels have been accessed rarely, generally by direct approach. For example, some diagnostic procedures involve direct cannulation of peripheral lymphatic vessels, e.g., to infuse dye for identification of lymph nodes. Direct access of the central lymphatic vessels, such as the thoracic duct, is generally avoided. A defect, for example, in the thoracic duct generally does not readily close on its own, leading to significantly morbid conditions, such as chylothorax (persistent collection of lymphatic fluid around the lungs).

The lymphatic system does, however, eventually drain into the vasculature. A majority of lymphatic vessels come to a confluence in the thoracic duct which generally enters the venous system at the junction of the left subclavian vein and the left internal jugular vein. A series of valves generally facilitate one-way flow of lymphatic fluid into the venous system and prevent reflux of whole blood into the thoracic duct. Although not well studied, disruption of one or more of these valves may have negative consequences. Therefore, it may be desirable to protect these valves and/or the lymphatic vessels themselves from damage.

Given the location of the thoracic duct, it may be feasible and desirable to access the lymphatic system by isolating or cannulating the thoracic duct via the venous system. Accessing the lymphatic vessels and removing and processing lymphatic fluid may be achieved using specialized catheter-based systems, as described elsewhere herein. Venous access may be achieved from any suitable location, including the left or right internal or external jugular, subclavian, axillary, anterior cubital, or femoral veins. Navigation to the thoracic duct may be aided by ultrasound, fluoroscopy, direct visualization, MRI, CT, and/or other imaging.

When accessing the lymphatic system trans-venously, it may be desirable to substantially isolate the thoracic duct or other lymphatic vessel, e.g., in order to selectively remove lymphatic fluid without removing significant amounts of whole blood, and/or to introduce fluids, agents, and the like selectively into the lymphatic vessels. It may also be desirable to selectively remove a portion of lymphatic fluid that is unneeded or pathologic and re-infuse the remaining portion back into the body.

Potential clinical applications may include drainage of lymphatic fluid for treatment of volume overload, for example, in the setting of congestive heart failure, depletion of lymphocytes or other immune system constituents, for example, in the setting of auto-immune disorders, preparation for transplantation procedures, treatment of infections residing primarily in immune-mediating cells, decompression of the lymphatic system to facilitate closure of leaking lymphatic vessels, treatment of lymphatic obstruction, and/or to otherwise remove fluid volume or pathologic constituents of lymphatic fluid. Further clinical applications may include diagnosis and/or monitoring of malignancy or metastatic spread of malignant cells, or treatment of infection or malignancy, for example, by infusion of antibiotic, antiviral, antiparisitic, and/or chemotherapeutic agents directly into the lymphatic system. Other applications may include rapid immunization by direct introduction of antigens and/or antigenic material into the lymphatic system, or other applications where sampling or removal of lymphatic fluid or infusion of diagnostic or therapeutic agents is beneficial.

In accordance with an exemplary embodiment, a system is provided for performing a medical procedure via a thoracic duct of a patient's body that includes a catheter or other tubular member including a proximal end, a distal end sized for introduction into a body lumen, and an aspiration lumen extending from the proximal end to a port in the distal end. An expandable member may be provided on the distal end, e.g., sized and/or shaped for substantially isolating the thoracic duct when expanded within the body lumen or thoracic duct itself. One or more external components may be coupled to the proximal end of the tubular member, e.g., a source of vacuum for removing fluid within the body lumen via the port and aspiration lumen, a detector for analyzing the fluid removed from the body lumen to identify lymphatic fluid, a separator for separating the lymphatic fluid or components of the lymphatic fluid from other fluid in the fluid removed from the body lumen, and/or a container for collecting the lymphatic fluid or components of the lymphatic fluid separated from other fluid.

In accordance with another embodiment, a method is provided for performing a medical procedure within a patient's body that includes a thoracic duct including an ostium communicating with the patient's venous system. A distal end of a tubular member may be introduced through the patient's venous system into a body lumen adjacent the ostium of the thoracic duct. An expandable member on the distal end of the tubular may be expanded adjacent the ostium, e.g., within the body lumen or the thoracic duct itself, and used to substantially isolate the thoracic duct from the body lumen, whereupon a medical procedure may be performed via the thoracic duct. For example, lymphatic fluid may be removed from the thoracic duct through a lumen of the tubular member and/or one or more agents may be introduced into the thoracic duct through the tubular member.

In an exemplary embodiment, fluid may be removed from the patient's body through a lumen of the tubular member, and the removed fluid may be analyzed to determine whether the fluid comprises lymphatic fluid or blood. For example, if the fluid comprises blood, the thoracic duct may not be isolated from the body lumen, and the removal of fluid may be stopped and/or the fluid may be directed to a waste container. If the fluid is lymphatic fluid, the fluid may be directed to a storage container, or components of the lymphatic fluid may be separated from other components of the fluid, and the separated components may be directed to a storage container. Optionally, the stored lymphatic fluid or the separated components of the lymphatic fluid may be infused back into the patient's body, if desired.

Other aspects and features of the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments of the invention, in which.

DETAILED DESCRIPTION OF THE EXEMPLARY EMBODIMENTS

Figure 1:
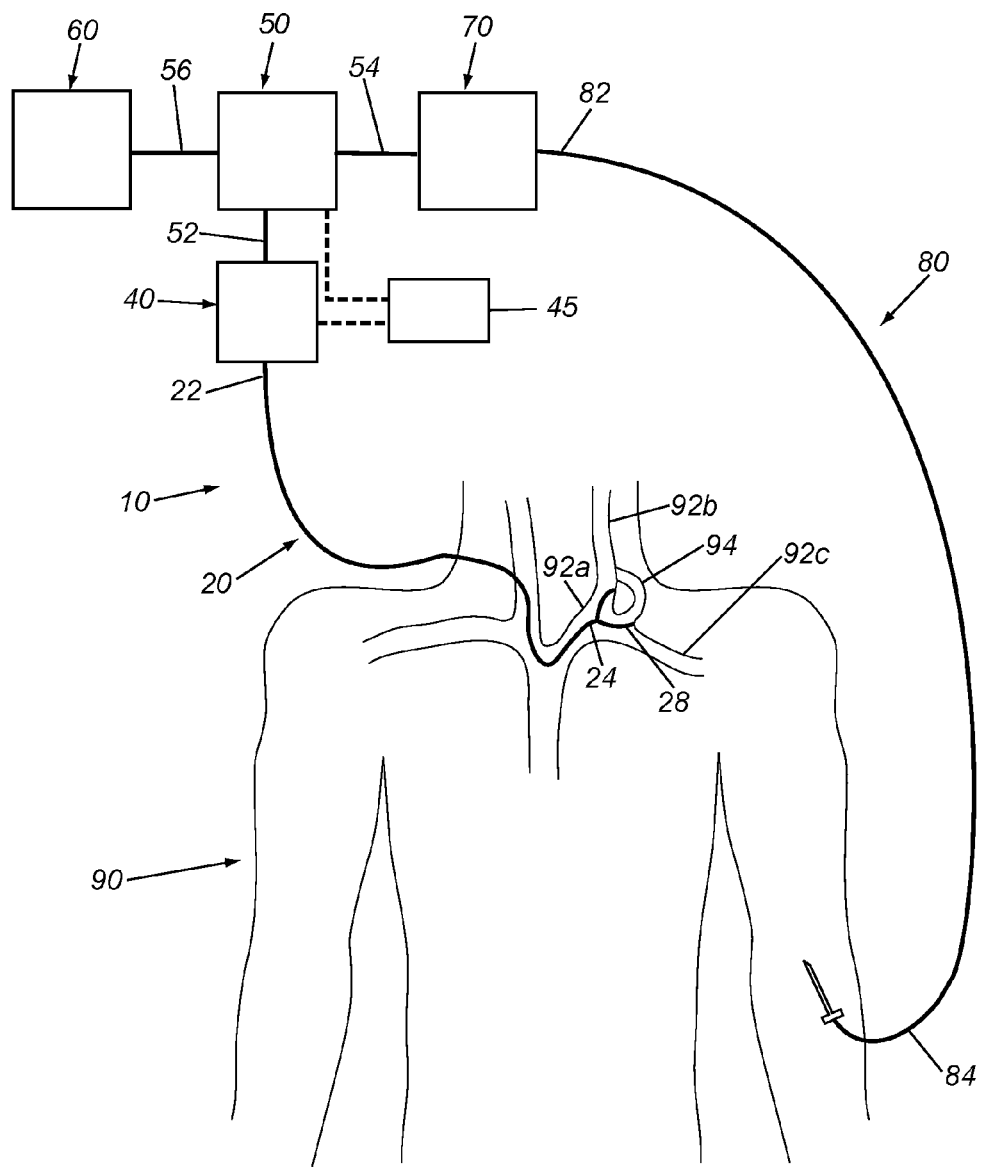
FIG. 1 is a detail of a patient's body showing a schematic of an exemplary system for accessing the lymphatic system of the patient.
Figure 2A:
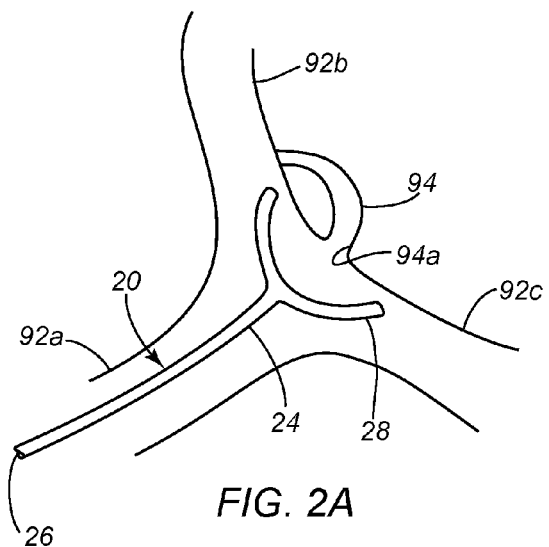
FIG. 2A is a detail of the junction of a thoracic duct of the lymphatic system with the venous system of a patient, showing an exemplary embodiment of a catheter for isolating and/or accessing the thoracic duct.

Turning to FIGS. 1 and 2A, an exemplary embodiment of a system 10 for isolating and/or accessing the lymphatic system of a patient 90 is shown. Generally, the system 10 may include a catheter 20 that includes a proximal end 22, a distal end 24, and one or more lumens 26 extending therebetween, e.g., an aspiration or infusion lumen 26 communicating with a port 27. Generally, the distal end 24 may be sized for introduction into a body lumen, e.g., one or more veins 92, such as the brachiocephalic vein 92a, jugular vein 92b, or subclavian vein 92c, and/or the thoracic duct 94 (best seen in FIG. 2B). In addition, the catheter 20 may include one or more features on the distal end 24 for facilitating isolating and/or accessing the thoracic duct 94.

Figure 2B:
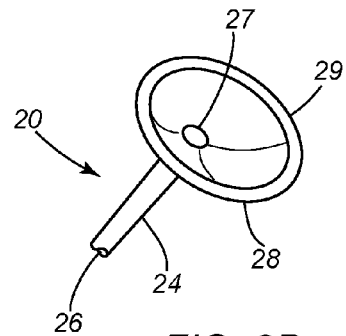
FIG. 2B is a perspective view of the catheter shown in FIG. 2A.

For example, as shown in FIGS. 2A and 2B, a catheter 20 is shown that includes an expandable hood 28 on the distal end 24 for isolating the thoracic duct 94, as described further below. In an exemplary embodiment, the hood 28 may be biased to an enlarged condition, such as that shown in FIGS. 2A and 2B, yet may be resiliently compressible to a contracted condition, e.g., to facilitate introduction of the hood 28 into the patient's vasculature. In this embodiment, the catheter 20 may include a constraint, e.g., a slidable outer sheath (not shown) that may overlie the hood to maintain the hood 28 in the contracted condition, e.g., for introduction into the patient's body lumen. The sheath or other constraint may be selectively removable such that the hood may automatically expand to the enlarged condition when deployed from the constraint.

Alternatively, the hood 28 may be mechanically expandable, e.g., using an actuator (not shown) on the proximal end 22 of the catheter 20 to expand a cage, wires, and/or other supports (also not shown) on the hood 28. In another alternative, the hood 28 may include an annular balloon extending around an outer periphery 29 of the hood 28, and the catheter 20 may include an inflation lumen (not shown) extending between the proximal and distal ends 22, 24 and communicating with the balloon. Inflation media may be delivered into and evacuated from the balloon to selectively expand and collapse the hood 28, as desired.

Figure 4A:
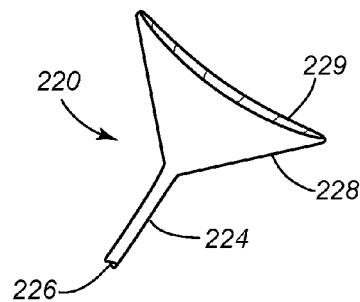
FIGS. 4A and 4B are perspective and cross-sectional views, respectively, of yet another embodiment of a catheter for isolating and/or accessing the thoracic duct.
Figure 4B:
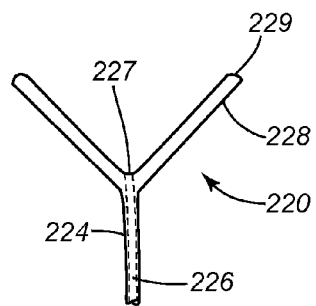

In the enlarged condition, the hood 28 may have a conical or other tapered shape extending inwardly from the periphery 29 to the distal end 24 of the catheter 20, e.g., to facilitate sealing the thoracic duct 94 and/or directing fluid into the port 27 of the catheter 20. Alternatively, as shown in FIGS. 4A and 4B, the hood 228 may have a saddle or other organic shape in the enlarged condition, e.g., defining an outer periphery 229 that may be shaped similarly to the wall of the vessels adjacent the thoracic duct 94. In addition or alternatively, the outer periphery 29 of the hood 28 may include compliant and/or resilient material, e.g., elastomeric material (not shown), to enhance a seal between the hood 28 and the wall of a vessel within which the hood 28 is deployed.

Figure 3A:
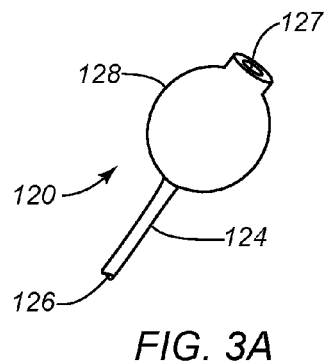
FIGS. 3A and 3B are perspective and cross-sectional views, respectively, of another embodiment of a catheter for isolating and/or accessing the thoracic duct.
Figure 3B:
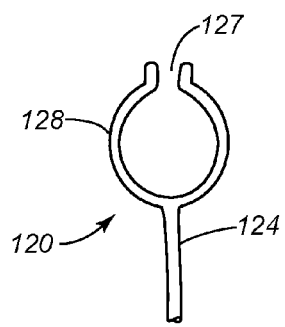

FIGS. 3A and 3B show another alternative embodiment of a catheter 120 that includes an expandable balloon 128 on a distal end 124 thereof. In this embodiment, the catheter 120 may include an inflation lumen (not shown) extending between a proximal end (also not shown) and the distal end 124 that communicates within an interior of the balloon 128 for selectively expanding and collapsing the balloon 1288. As shown, the balloon 128 may be expanded to a substantially spherical shape in the enlarged condition that tapers to a nipple providing the port 127 that extends beyond the balloon 128. Alternatively, the distal end 124 of the catheter 120 may extend through the balloon 128 to define the port 127. Optionally, the port 127 may be formed from resilient and/or flexible material, e.g., to facilitate substantially atraumatic advancement of the port 127, e.g., into the ostium of the thoracic duct 94, as described further below.

Optionally, in any of these embodiments (with reference to the catheter 10 of FIGS. 2A and 2B merely for convenience), additional features may be provided on the distal end 24 or otherwise on the catheter 20. For example, an imaging element and/or illumination element (not shown) may be provided on the distal end 24 to allow imaging within the patient's body, e.g., to facilitate identification and/or isolation of the thoracic duct 94 (for example, blood may obscure imaging beyond the distal end 24, while lymphatic fluid, which is substantially clear, may not, thereby providing confirmation when the thoracic duct 94 is substantially isolated, as described further below). In addition, the catheter 24 may include an infusion lumen (not shown) separate from the lumen 26, e.g., to allow infusion of fluids or agents independent of aspiration or removal of fluid through the lumen 26.

In addition or alternatively, the distal end 24 may include one or more steering elements (not shown) and/or may be biased to a predetermined nonlinear shape, e.g., to facilitate location of the thoracic duct 94 and/or introduction of the distal end 24 into the ostium of the thoracic duct 94, as described further below. For example, the distal end 24 may be biased to a desired shape, e.g., including multiple curves and/or complex shapes, based on the anatomy encountered, or may be malleable or otherwise shapeable so the distal end 24 may be directed to a desired shape based on the particular anatomy involved before introduction into the patient's body. For example, the distal end 24 may include at least one first curve designed to position the tip of the distal end 24 in or near the thoracic duct 94 and at least one second curve designed to generate a force of apposition in order to achieve a substantial seal. In addition, one or more catheters may be arranged to telescope inside another (not shown), any of which may be shaped or steerable, if desired to facilitate introduction and/or isolation of the thoracic duct 94.

In another option, multiple expandable members (not shown) may be provided on the distal end 24. For example, a pair of spaced apart balloons or other expandable members may be provided, and an aspiration port may be located between the balloons. In this embodiment, fluid may be removed and/or delivered into the space between the balloons via the port and corresponding lumen of the catheter.

In addition or alternatively, one or more other features may be provided for maintaining apposition against the vessel wall and/or creating a seal, for example, hooks, suction cups, an expandable member or balloon pressing against an opposite wall, one or more elements for transmitting axial force to the catheter, and the like.

In addition to the catheter 20, the system 10 may include one or more external components for performing a medical procedure, e.g., which may involve removing lymphatic fluid from the patient's body 90 via the thoracic duct 94, introducing agents or devices (not shown) into the thoracic duct 94, and/or infusing the removed lymphatic fluid, components thereof, and/or other agents into other locations within the patient's body 90. For example, one or more external devices may be provided that are coupled to the proximal end 22 of the catheter 20, e.g., for detecting, separating, collecting, and/or infusing lymphatic fluid and/or other fluids, as described further below. The external components may be provided integrated into a single device or may be provided as separate discrete components that are coupled to one another (e.g., along a fluid path, electrically, and/or otherwise).

In the example shown in FIG. 1, the external components include a detector 40, a controller 45, a separator 50, a waste container 60, a storage container 70, and an infusion device 80. One or more of the components may include a pump or source of vacuum or pressure, e.g., for removing fluid from the patient's body and/or delivering fluid into the patient's body via the catheter 20, or infusing fluids via the infusion device 80, as described further below. In alternative embodiments, one or more of the components may be omitted. For example, the catheter 20 may simply be coupled directly to the storage container 70, e.g., with or without a source of vacuum to facilitate collection of lymphatic fluid.

Returning to FIG. 1, the detector 40 may be coupled to the proximal end 22 of the catheter 20, e.g., for receiving fluids that are drawn through the lumen 26 of the catheter 20 from the port 27 in the distal end 24. The detector 40 may include one or more sensors (not shown), e.g., for distinguishing between lymphatic fluid and blood. In exemplary embodiments, the sensor(s) may include one or more optical sensors (e.g., for detecting the presence of red blood cells by light transmission or reflection characteristics), chemical sensors (e.g., for detecting one or more of pH, oxygen concentration, lactate, leukocyte esterase, and the like), sensors for measuring hematocrit, electrical sensors (e.g., for measuring impedance), mechanical sensors (e.g., for detecting pressure waves, which may differ between the venous system and the thoracic duct; for flow detection, e.g., by Doppler ultrasound), filter devices sized to constituents of whole blood, and the like. In addition or alternatively, a sensor may be provided that is adapted to detect the presence of an exogenous marker introduced into the lymphatic system, such as a dye (e.g., methylene blue), an ingested marker, a fluorescent marker, and the like.

For example, a pump or other source of vacuum or pressure (not shown) within or coupled to the detector 40 may be selectively activated, e.g., by the controller 45 (or alternatively manually by a user, if desired), to remove fluid from the patient's body via the catheter 20 through the detector 40 to the separator 50. The controller 45 may automatically analyze sensor data from the sensors to identify whether the fluid is lymphatic fluid, blood, or other fluid.

For example, if the controller 45 determines that the fluid includes blood, the controller 45 may direct the fluid to the waste container 60, e.g., through the separator 50 or directly. In addition or alternatively, if the controller 45 detects the presence of a significant amount blood in the fluid (based on data from the detector 40 or otherwise) or detects a loss of seal (e.g., due a sudden pressure change in the fluid being removed via the catheter 20), the controller 45 may shut down the pump, close a shut-off valve (not shown) in the detector 40, or otherwise stop flow of fluid from the catheter 20 into the detector 40 and/or the rest of the system 10. This safety mechanism may be active, i.e., shut down automatically, or passive, i.e., merely warn the user.

In an exemplary embodiment, the separator 50 may include a valve including an inlet 54 that communicates with the detector 40, a first outlet 54 communicating with the storage container 70, and a second outlet communicating with the waste container 60. The valve being selectively operable between the first and second outlets by the controller 45, e.g., to direct undesired fluid, e.g., blood, to the waste container 60, and desired fluid, e.g., lymphatic fluid or components thereof, to the storage container 70. Alternatively, or in addition, the separator 50 may include one or more devices for separating various components of lymphatic fluid, including various types of cells, proteins, electrolytes, water, and/or other constituent parts of lymphatic fluid. For example, water may be substantially separated from other components in order to selectively remove excess water from a patient. As another example, pathologic cells may be selectively separated from other constituents in order to remove pathologic cells from a patient.

In an alternative embodiment, a filter (not shown) may be provided within the detector 40 or separator 50, which may clog in the presence of a predetermined number or concentration of cells, e.g., red blood cells, to prevent the fluid from being delivered into the storage container 70. In a further alternative, coagulation/clotting may be used to prevent flow in the presence of whole blood and its constituents (for example, platelets). For example, a passage through the detector 40 or other external component may be sized to clot spontaneously, a filter may be used where clotting decreases flow, and/or pro-coagulant materials may be used to augment or accelerate a clotting response. In such alternatives, the component of the system 10 designed to prevent flow may be cleanable and/or replaceable, e.g., to allow to resumption of flow after isolation of the thoracic duct 94 is reestablished.

If the controller 45 confirms that the fluid is lymphatic fluid, the controller 45 may activate the separator 50 to direct the lymphatic fluid or components of the lymphatic fluid into the storage container 70. For example, if the entire lymphatic fluid is to be collected, the separator 50 may simply divert the fluid into the storage container 70. Alternatively, it may be desirable to separate certain constituents of the removed fluid, e.g., lymphatic fluid, particular cells, proteins, and the like. For example, the separator 50 may include one or more of a mechanical filtration system, an osmotic gradient system, a concentration gradient system, a centrifuge, and the like to separate the desired components from the rest of the fluid. Once separated, the desired components may be delivered to the storage container 70, while the rest of the fluid is delivered to the waste container 60.

Optionally, the controller 60 or other components of the system 10 may monitor the flow to keep track of the amount of fluid extracted and/or to stop after a predetermined amount of fluid is extracted. In addition or alternatively, the controller 60 may operate the pump, vacuum source, valve, and/or other components of the system 10 periodically or otherwise intermittently, e.g., to allow reaccumulation of fluid within the lymphatic vessels.

In certain cases it may be desirable to re-infuse all or a portion of the lymphatic fluid removed, for example, all cells and/or proteins (e.g., discard fluid and retain the useful constituents of lymph), only a certain portion of removed cells and/or proteins, (e.g., discard harmful constituents and retain useful constituent), and/or other constituents of the removed lymphatic fluid. One approach may be simply to retain an initial volume of removed fluid that may have a higher concentration of cells, proteins, and the like compared to the subsequent volume removed. For example, there may be a relatively small initial volume of lymphatic fluid in the vessels that, upon sustained drainage, may be repleted with interstitial fluid having relatively few cells. Alternatively, filtration, separation, or other methods may be used to create a desirable portion for reinfusion.

For example, as shown in FIG. 1, an infusion catheter 80 may be provided that includes a proximal end 82 coupled to the storage container 70, and a distal end 84 sized for delivering the stored fluid into the patient's body 90.

As shown in FIGS. 1 and 2A, the system 10 may be used to perform a medical procedure within the patient's body 90 that includes the thoracic duct 94, which may be related to any of the conditions and/or treatments described elsewhere herein. Initially, the distal end 24 of the catheter 20 may be introduced into the patient's body 90, e.g., into the venous system from a percutaneous access site, such as the left or right internal or external jugular, subclavian, axillary, anterior cubital, or femoral veins. Navigation to the thoracic duct 94 may be aided using external imaging, such as ultrasound imaging. Optionally, the distal end 24 of the catheter 20 may include one or more echogenic features (not shown) to facilitate navigation under ultrasound. Such exemplary features may include doping or coating with tungsten, tungsten carbide, titanium dioxide, iron oxide, zinc oxide, platinum, gold, barium, bismuth, and/or titanium; echogenic surface modifications such as reflective gratings, surface depression and/or projections; inclusions, for example, of glass particles, air bubbles, etc.; or other methods for imparting echogenicity, including those described in U.S. Pat. No. 5,921,933, the entire disclosure of which is expressly incorporated by reference herein.

In addition or alternatively, other imaging may be used, such as fluoroscopy, MRI, CT, and/or direct visualization, e.g., using an imaging element carried on the distal end 24 of the catheter 20. Exemplary imaging elements and methods for using them are disclosed in U.S. Publication Nos. 2011/0034790, 2007/0015964, 2006/0084839, and 2004/0097788, the entire disclosures of which are expressly incorporated by reference herein.

The hood 28 (or any of the other expandable members described herein) on the distal end 24 of the catheter 20 may be expanded adjacent the ostium 94b, e.g., within the brachiocephalic vein 92a, and then used to substantially isolate the thoracic duct 94 from the adjacent veins 92. For example, with the hood 28 expanded, the catheter 20 may be advanced to press the hood 28 against the wall of the veins 92 adjacent the ostium 94b, thereby providing a substantially fluid-tight seal.

If desired, an initial bolus of fluid may be removed through the catheter 20 to detect the presence of blood, remove any residual blood that may be captured within the hood 28, and/or to confirm the seal. Optionally, a bolus of fluid may be delivered through the catheter 20 into the hood 28, e.g., to clear away residual blood or undesired fluid. In addition or alternatively, one or more sensors (not shown) may be provided on the distal end 24 of the catheter 20, e.g., instead of or in addition to the detector 40, which may allow earlier detection and/or to facilitate navigation to the thoracic duct 94.

Once the thoracic duct 94 is substantially isolated, a medical procedure may be performed via the thoracic duct 94. For example, lymphatic fluid may be removed from the thoracic duct 94 through the lumen 26 of the catheter 20 and/or one or more agents may be introduced into the thoracic duct 94, e.g., through the lumen 26 or another lumen of the catheter 20. In an exemplary embodiment, the removed fluid may be analyzed to determine whether the fluid comprises lymphatic fluid or blood. For example, if the fluid comprises blood, the thoracic duct 94 may not be isolated from the veins 92, the fluid may be directed to the waste container 60. If the fluid is lymphatic fluid, the fluid may be directed to the storage container 70, or components of the lymphatic fluid may be separated from other components of the fluid, e.g., by the separator 50, and the separated components may be directed to the storage container 70. Optionally, the stored lymphatic fluid or the separated components of the lymphatic fluid may be infused back into the patient's body, e.g., via the infusion catheter 80, as described elsewhere herein.

Once sufficient fluid has been removed, the hood 28 may be collapsed and the catheter 20 removed from the patient's body 90.

Figure 5A:
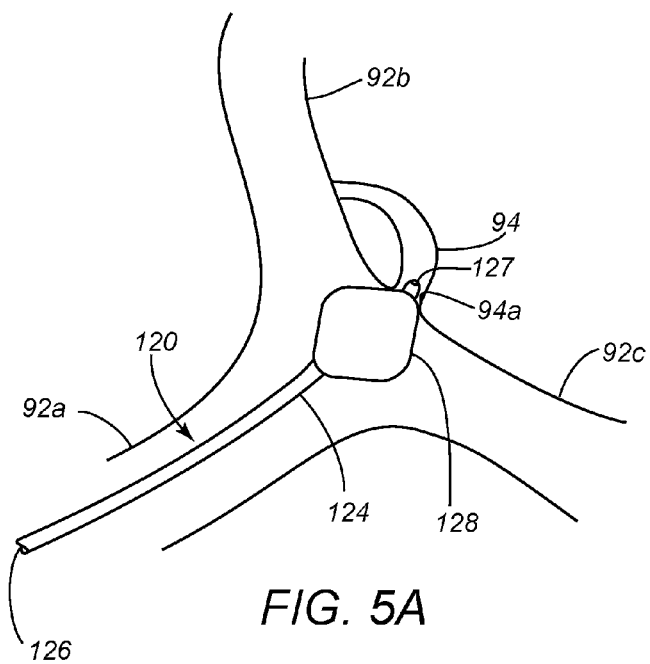
FIGS. 5A and 5B are details of the junction of the thoracic duct with the venous system, showing alternative apparatus and methods for isolating and/or accessing the thoracic duct.
Figure 5B:
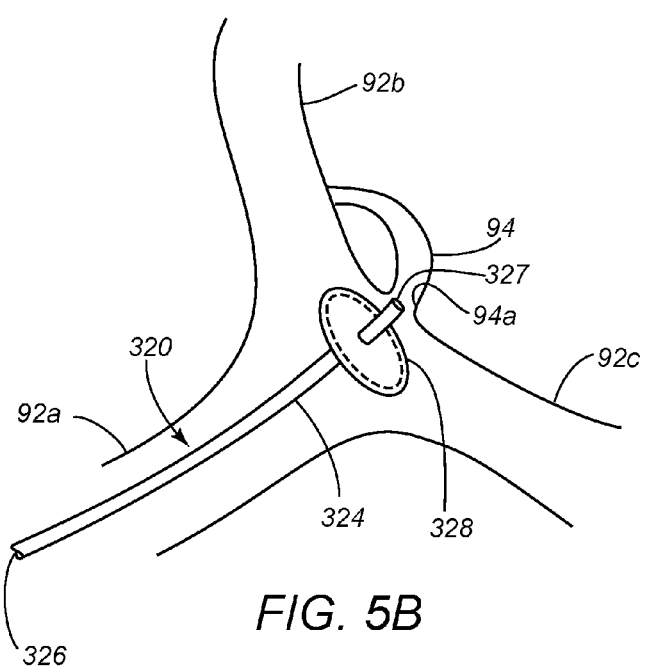

Turning to FIGS. 5A and 5B, alternative embodiments of catheters and methods are shown for isolating the thoracic duct 94. In the embodiment of FIG. 5A, the balloon 128 may limit the distance that the port 127 enters the ostium 94a of the thoracic duct 94, e.g., to reduce the risk of damage to a valve (not shown) in the thoracic duct 94. Because the balloon 128 has a tapered distal surface, the port 127 may enter a short distance into the thoracic duct 94. In contrast, FIG. 5B shows a catheter 320 that includes an expandable member 328 having a disk or ring shape that limits insertion of the port 127. In further alternatives, the catheter 328 (or other embodiments herein) may include one or more other features (not shown) that engage the thoracic duct ostium 94a to limit insertion of the port 327. For example, a distal tip of the catheter may include a compliant wedge, a foam seal, elastomeric material, expanded PTFE, and the like. In addition or alternatively, the tip of the catheter 328 may include a relatively small compliant ring, e.g., doughnut of silicone and the like (not shown), to serve as a stopper or seal.

Figure 6:
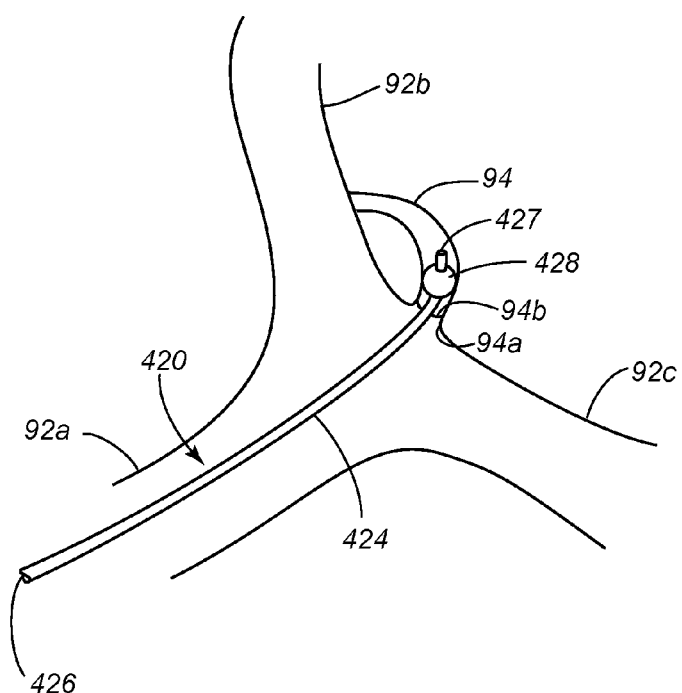
FIG. 6 is a detail of the junction of the thoracic duct with the venous system, showing another alternative apparatus and method for isolating and/or accessing the thoracic duct.

Turning to FIG. 6, another embodiment of a catheter 420 is shown that includes a distal end 424 and balloon 428 sized to be introduced into the thoracic duct 94. For example, as shown, the distal end 424 may be advanced beyond a valve 94b in the thoracic duct 94 such that the balloon 428 may be inflated beyond the valve 94b. In addition or alternatively, the catheter 420 may include one or more other features for securing and/or sealing distal to a valve, including one or more compliant rings, radial filaments/brushes, and/or other passive fixation devices (not shown) that may at least partially resist retraction or avoid spontaneous dislodgement of the catheter 420 during use. In addition or alternatively, active fixation, such as suction, may be used to substantially fix the distal end 428 of the catheter 420 at a desired location, e.g., within the thoracic duct 94.

In addition to the trans-venous approaches described elsewhere herein, it may also be possible to directly cannulate a lymphatic vessel and/or associated lymph node in order to access lymphatic system using any of the systems and methods herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for performing a medical procedure via a thoracic duct of a patient's body, comprising:
    a tubular member comprising a proximal end, a distal end sized for introduction into a body lumen, an aspiration lumen extending from the proximal end to a port in the distal end, an expandable member on the distal end sized for substantially isolating the thoracic duct when expanded within the thoracic duct, and an actuator on the proximal end of the tubular member to selectively expand and collapse the expandable member when the proximal end is external to the patient's body;
    one or more external devices configured to be located external to the patient's body for removing fluid within the thoracic duct from the patient's body, comprising:
    a detector for analyzing the fluid removed from the thoracic duct via the aspiration lumen to identify whether blood is present in the removed fluid;
    a container coupled to the proximal end of the tubular member for collecting fluid removed from the thoracic duct via the aspiration lumen; and
    a controller coupled to the detector for opening a fluid path between the aspiration lumen and the container when the detector confirms that the fluid removed via the aspiration lumen does not include whole blood.

2. The system of claim 1, wherein the one or more external devices comprises a separator coupled to the proximal end of the tubular member for separating the lymphatic fluid or components of the lymphatic fluid from other fluid in the fluid removed from the thoracic duct, and wherein the separator comprises a valve comprising an inlet that receives fluid from the tubular member, a first outlet for directing the lymphatic fluid or components of the lymphatic fluid to the container, and a second outlet for directing other fluids to a waste container, the valve being selectively operable between the first and second outlets.

3. The system of claim 2, wherein the separator comprises at least one of a mechanical filtration system, an osmotic gradient system, a concentration gradient system, and a centrifuge.

4. The system of claim 1, wherein the detector comprises one or more sensors that comprise at least one of an optical sensor that detects the presence of red blood cells by light transmission or reflection characteristics, a chemical sensor that detects one or more of pH, oxygen concentration, lactate, and leukocyte esterase, a sensor that measures hematocrit, an electrical sensor that measures impedance, a mechanical sensor that detects pressure waves that differ between the venous system and the thoracic duct, and a Doppler ultrasound sensor.

5. The system of claim 1, wherein the expandable member comprises a balloon, wherein the actuator comprises a source of inflation media, and wherein the tubular member comprises an inflation lumen for delivering inflation media from the source of inflation media into and out of the balloon for selectively expanding and collapsing the balloon.

6. The system of claim 5, wherein the tubular member terminates in a flexible distal tip beyond the balloon.

7. The system of claim 1, further comprising a source of vacuum coupled to the proximal end of the tubular member and communicating with the aspiration lumen for removing fluid within the thoracic duct via the port and aspiration lumen, wherein the controller is coupled to the source of vacuum to activate the source of vacuum when the detector confirms that the fluid removed via the aspiration lumen does not include whole blood.

8. The system of claim 7, wherein the controller is configured to deactivate the source of vacuum when the detector indicates that the fluid removed from the thoracic duct includes whole blood to stop fluid flow from the tubular member.

9. The system of claim 7, wherein the controller is configured to deactivate the source of vacuum when the detector indicates a sudden change in pressure in the fluid being removed via the aspiration lumen to stop fluid flow from the tubular member.

10. The system of claim 1, further comprising an infusion device comprising a proximal end communicating with the container and a distal end sized for delivering one or more components of the lymphatic fluid back into the patient's body.

11. The system of claim 1, further comprising a valve associated with the detector, wherein the controller is coupled to the valve to open the valve when the detector confirms that the fluid removed via the aspiration lumen does not include whole blood, thereby opening the fluid path between the aspiration lumen and the container.

12. A method for performing a medical procedure within a patient's body, the body comprising a thoracic duct including an ostium communicating with the patient's venous system, comprising:
    introducing a distal end of a tubular member through the patient's venous system into a body lumen adjacent the ostium of the thoracic duct such that a proximal end of the tubular member remains external to the patient's body;

inserting the distal end into the thoracic duct such that an expandable member on the distal end of the tubular member is positioned beyond a valve of the thoracic duct;

expanding the expandable member within the thoracic duct beyond the valve to substantially isolate the thoracic duct from the body lumen; and performing a medical procedure via the thoracic duct, wherein performing a medical procedure comprises:

activating a source of vacuum to remove fluid within the thoracic duct via the tubular member;

analyzing the removed fluid to determine whether the removed fluid contains whole blood;

if the removed fluid includes whole blood, deactivating the source of vacuum to stop fluid flow from the thoracic duct; and if the removed fluid does not include whole blood, directing the removed fluid to a container external to the patient's body.

13. The method of claim 12, wherein the medical procedure comprises removing lymphatic fluid from the thoracic duct through a lumen of the tubular member to a location external to the patient's body.

14. The method of claim 13, further comprising infusing one or more components of the removed lymphatic fluid back into the patient's body.

15. The method of claim 13, wherein one or more components of the removed lymphatic fluid are infused back into the patient's body via an infusion device introduced into the patient's body.

16. The method of claim 12, wherein the percutaneous access site is one of a left or right internal or external jugular, subclavian, axillary, anterior cubital, or femoral vein of the patient's body.

17. The method of claim 12, wherein performing a medical procedure comprises:

activating a source of vacuum to remove fluid within the thoracic duct via the tubular member; and deactivating the source of vacuum when a sudden change in pressure in the fluid being removed is detected to stop fluid flow from the tubular member.

18. The method of claim 12, wherein performing a medical procedure comprises:

activating a source of vacuum to remove fluid within the thoracic duct via the tubular member; and emitting a warning when a sudden change in pressure in the fluid being removed is detected to stop fluid flow from the tubular member.

19. The method of claim 12, wherein the medical procedure comprises introducing one or more agents into the thoracic duct through a lumen of the tubular member.

20. The method of claim 12, wherein the body lumen comprises a brachiocephalic vein.

21. The method of claim 12, further comprising separating components of the lymphatic fluid from other components of the fluid external to the patient's body.

22. The method of claim 21, wherein the medical procedure further comprises directing the separated components of the lymphatic fluid to a storage container.

23. The method of claim 21, wherein the medical procedure further comprises infusing the separated components of the lymphatic fluid into the patient's body.

24. The method of claim 12, wherein the distal end of the tubular member is introduced into the patient's venous system from a percutaneous access site.

25. The method of claim 24, further comprising removing the tubular member from the patient's body via the percutaneous access site after performing the medical procedure.

26. The method of claim 12, further comprising using external ultrasound imaging during navigation of the distal end of the tubular member through the patient's venous system.

27. The method of claim 26, wherein the distal end of the tubular member comprises one or more echogenic features to facilitate navigation of the distal end while using the ultrasound imaging.

* * * * *